(12) United States Patent
Kawabe et al.

(10) Patent No.: US 10,300,215 B2
(45) Date of Patent: May 28, 2019

(54) NEEDLE ASSEMBLY

(71) Applicant: NIPRO CORPORATION, Osaka-shi, Osaka (JP)

(72) Inventors: Minami Kawabe, Osaka (JP); Tomoe Morita, Osaka (JP)

(73) Assignee: NIPRO CORPORATION, Osaka (JP)

( * ) Notice: Subject to any disclaimer, the term of this patent is extended or adjusted under 35 U.S.C. 154(b) by 17 days.

(21) Appl. No.: 15/329,540

(22) PCT Filed: Jun. 24, 2015

(86) PCT No.: PCT/JP2015/068246
§ 371 (c)(1),
(2) Date: Jan. 26, 2017

(87) PCT Pub. No.: WO2016/021323
PCT Pub. Date: Feb. 11, 2016

(65) Prior Publication Data
US 2017/0216534 A1 Aug. 3, 2017

(30) Foreign Application Priority Data

Aug. 4, 2014 (JP) .................................. 2014-159079

(51) Int. Cl.
*A61M 5/32* (2006.01)
*A61M 5/50* (2006.01)

(52) U.S. Cl.
CPC ........ *A61M 5/3213* (2013.01); *A61M 5/3202* (2013.01); *A61M 5/3269* (2013.01); *A61M 5/50* (2013.01); *A61M 2005/3249* (2013.01)

(58) Field of Classification Search
CPC .. A61M 5/3202; A61M 5/3269; A61M 5/327; A61M 2005/3249; A61M 2005/3424
See application file for complete search history.

(56) References Cited

U.S. PATENT DOCUMENTS

| 4,804,371 A | 2/1989 | Vaillancourt |
| 5,026,356 A | 6/1991 | Smith |
| (Continued) | | |

FOREIGN PATENT DOCUMENTS

| EP | 1350529 A1 | 10/2003 |
| JP | H10-127767 A | 5/1998 |
| (Continued) | | |

OTHER PUBLICATIONS

Mar. 5, 2018 extended Search Report issued in European Patent Application No. 15829708.5.

(Continued)

*Primary Examiner* — Laura A Bouchelle
(74) *Attorney, Agent, or Firm* — Oliff PLC

(57) ABSTRACT

A needle assembly includes a needle hole having an inside diameter that is greater than an outside diameter of a needle, and by a moving-side guide integrally provided to a needle tip cover being engaged with a fixed-side guide fixedly provided to the needle, a guide mechanism is provided to guide the needle tip cover from a proximal end side towards a distal end side of the needle while maintaining a state of noncontact with the needle, and to guide the needle tip cover to a position where the needle tip cover covers the needle tip while deviating the needle tip cover in a direction in which the needle hole goes away from a center axis of the needle at a position beyond the needle tip, and avoiding contact of the needle tip with the needle hole.

8 Claims, 10 Drawing Sheets

(56) References Cited

U.S. PATENT DOCUMENTS

| | | | |
|---|---|---|---|
| 5,411,492 A | | 5/1995 | Sturman et al. |
| 5,672,161 A | * | 9/1997 | Allen .................. A61M 5/3202 604/192 |
| 2004/0243066 A1 | | 12/2004 | Meyer |
| 2005/0159706 A1 | | 7/2005 | Wilkinson et al. |
| 2007/0232998 A1 | | 10/2007 | Yang et al. |

FOREIGN PATENT DOCUMENTS

| | | |
|---|---|---|
| JP | 2003-299735 A | 10/2003 |
| JP | 2005-501665 A | 1/2005 |
| WO | 2009/067531 A1 | 5/2009 |

OTHER PUBLICATIONS

Feb. 7, 2017 International Preliminary Report on Patentability issued in International Patent Application No. PCT/JP2015/068246.
Aug. 4, 2015 International Search Report issued in International Patent Application No. PCT/JP2015/068246.
Nov. 21, 2018 Office Action issued in Japanese Patent Application No. 2016-540109.
Aug. 20, 2018 Office Action issued in Japanese Patent Application No. 2016-540109.

* cited by examiner

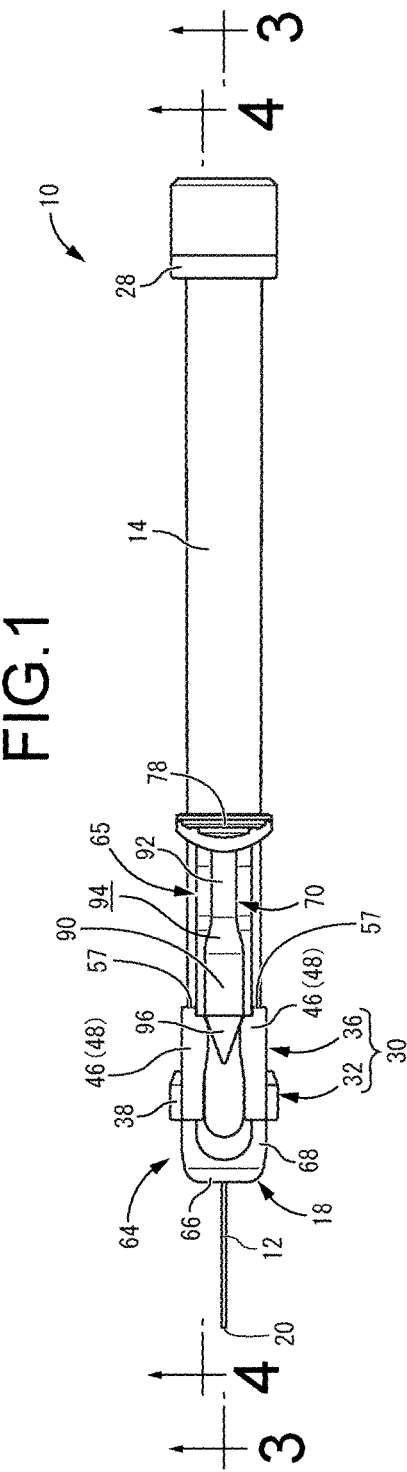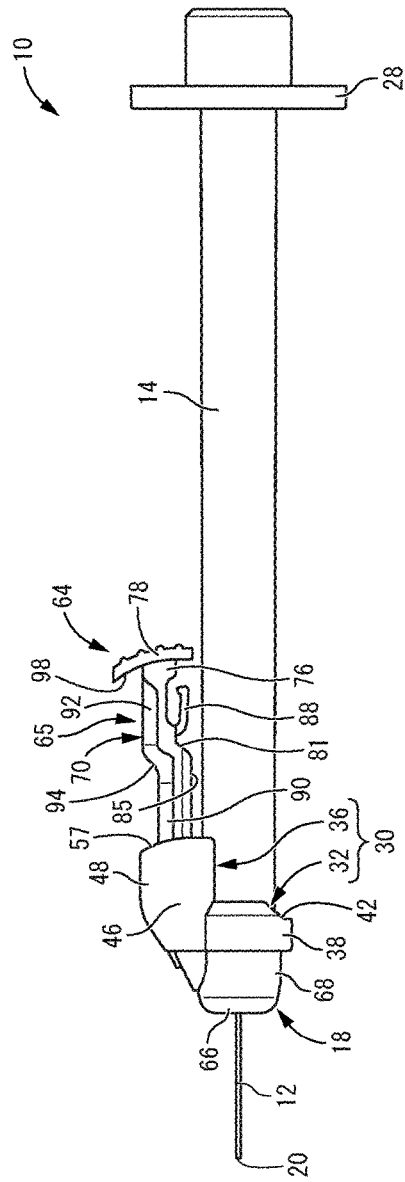

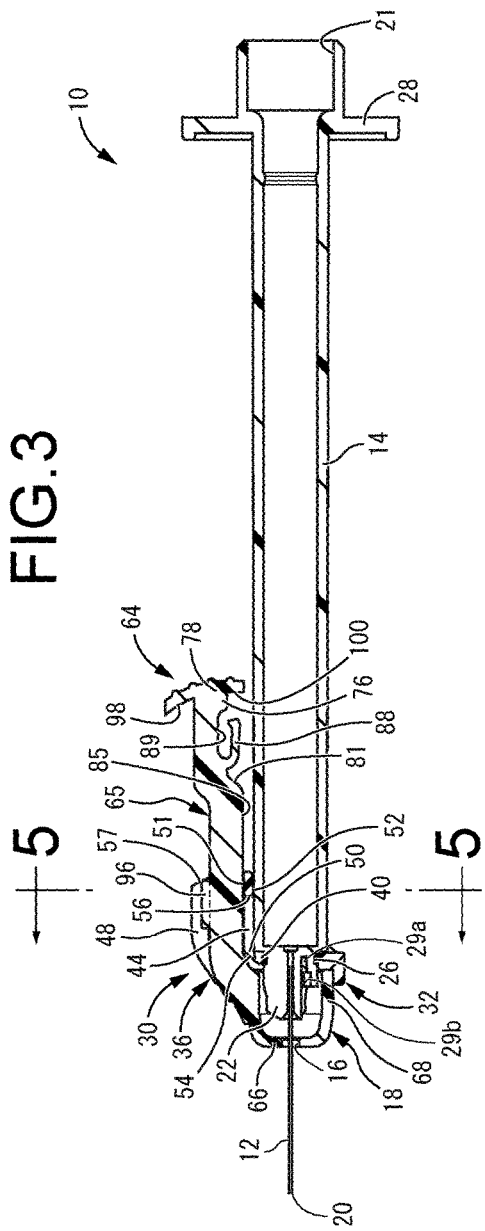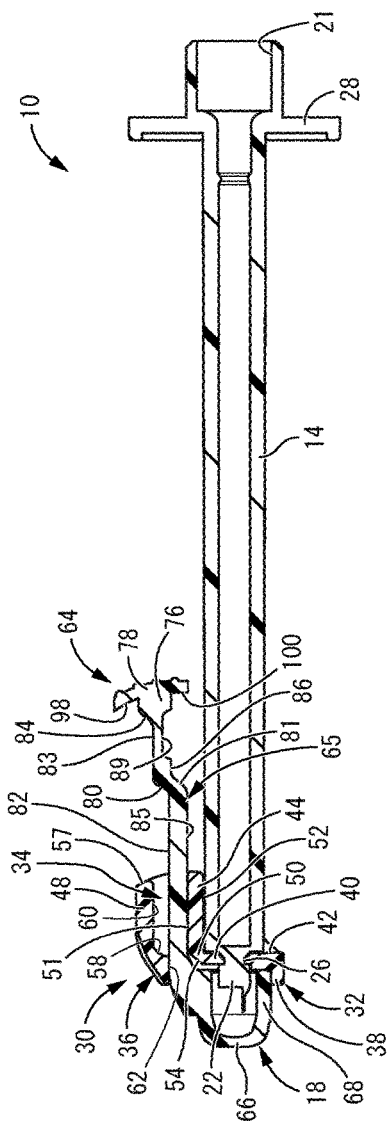

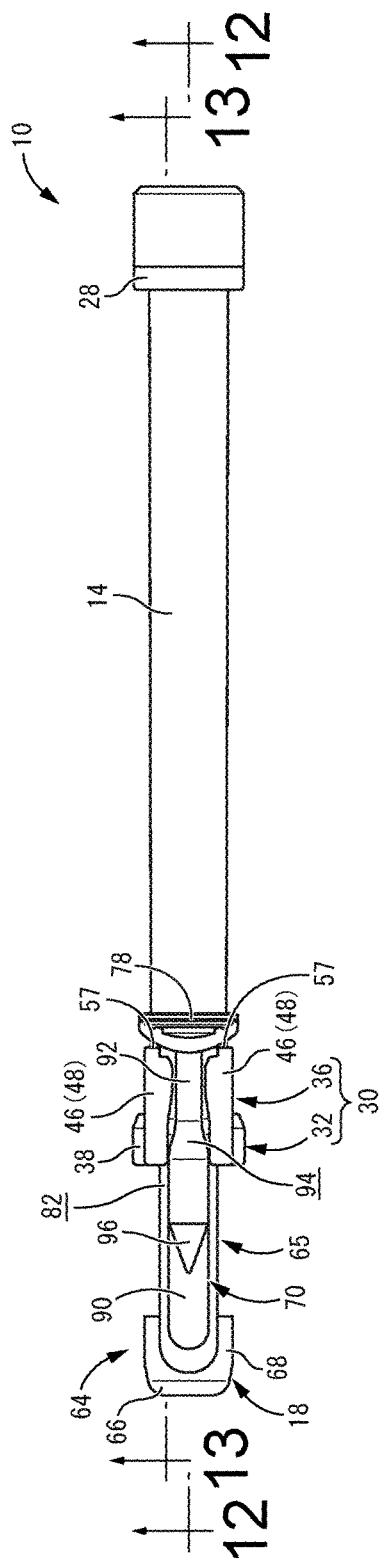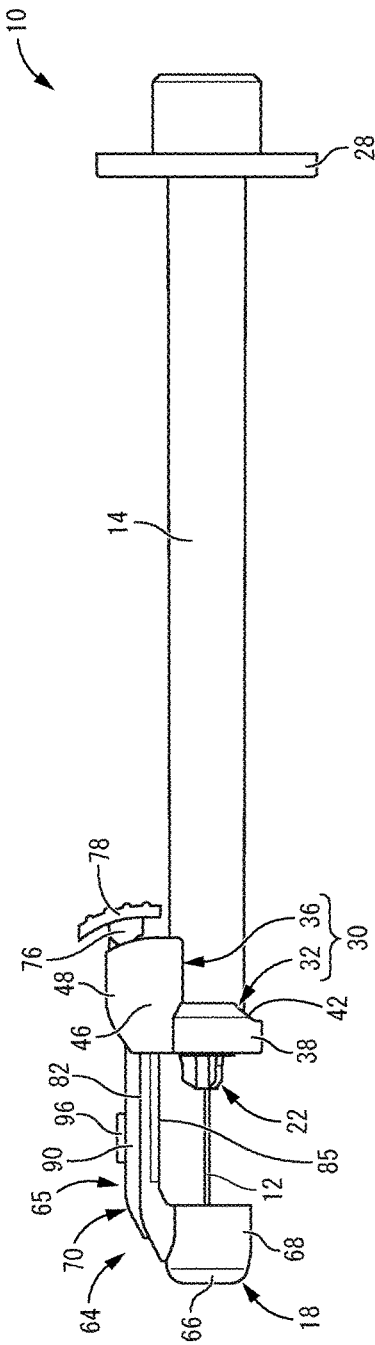

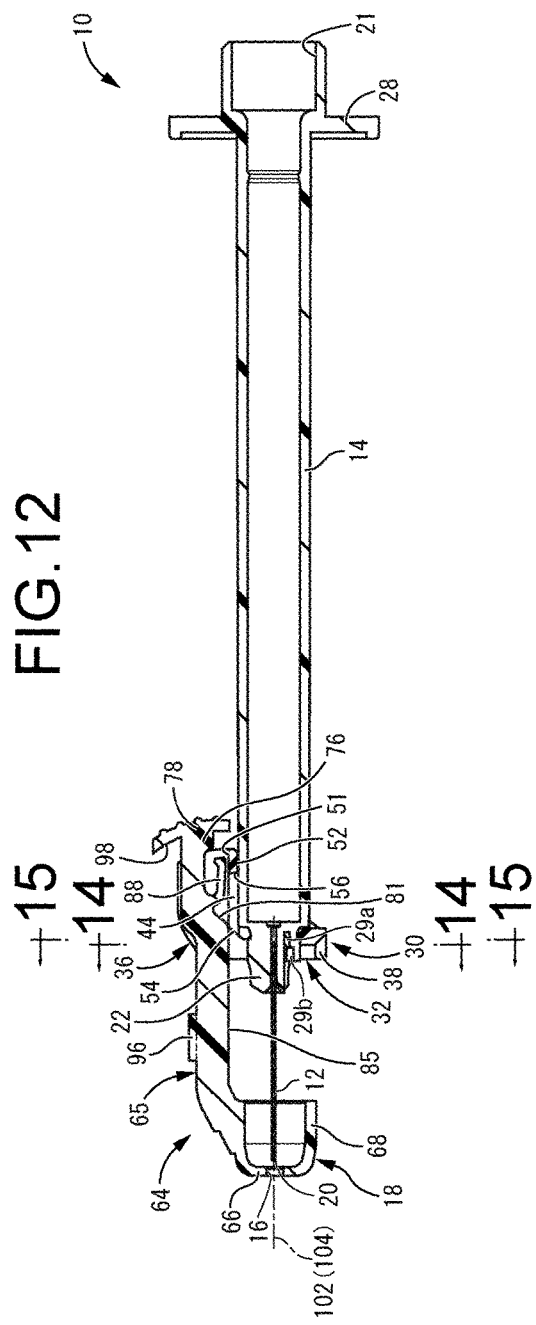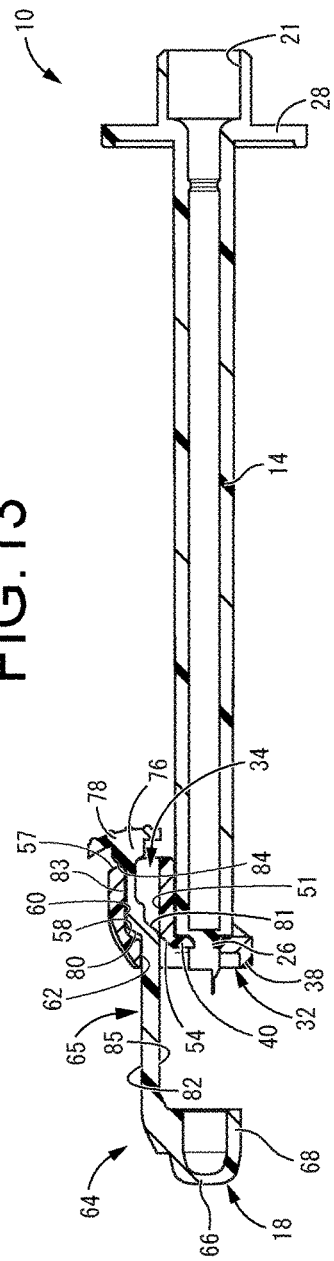

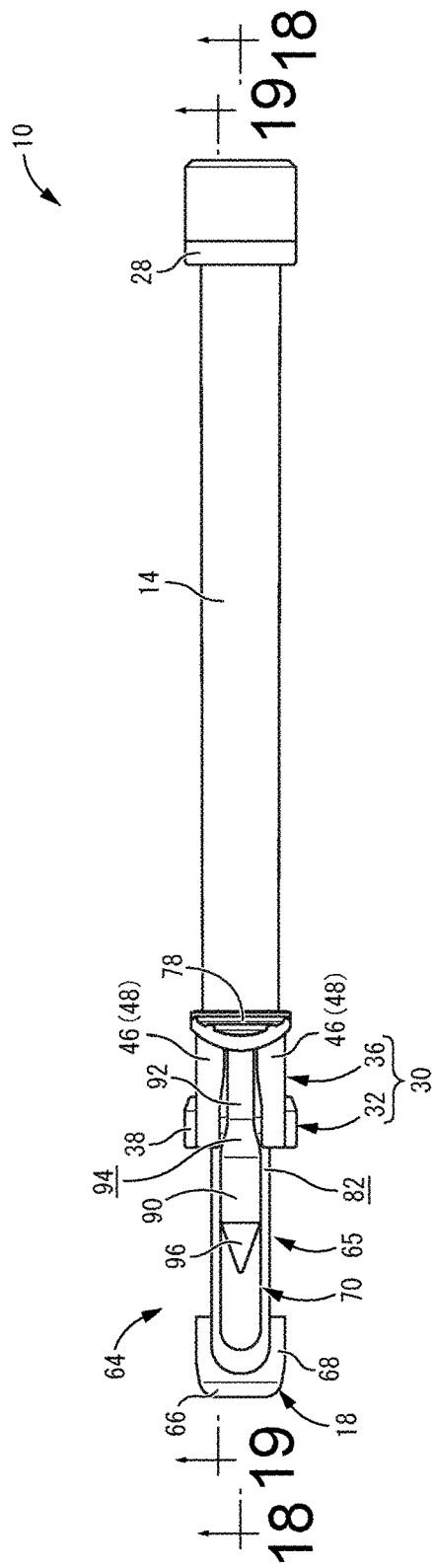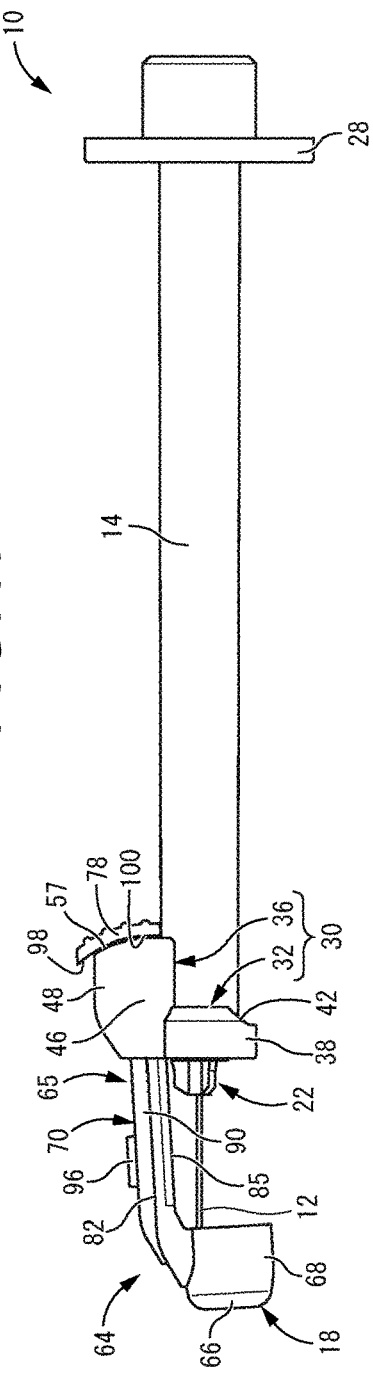

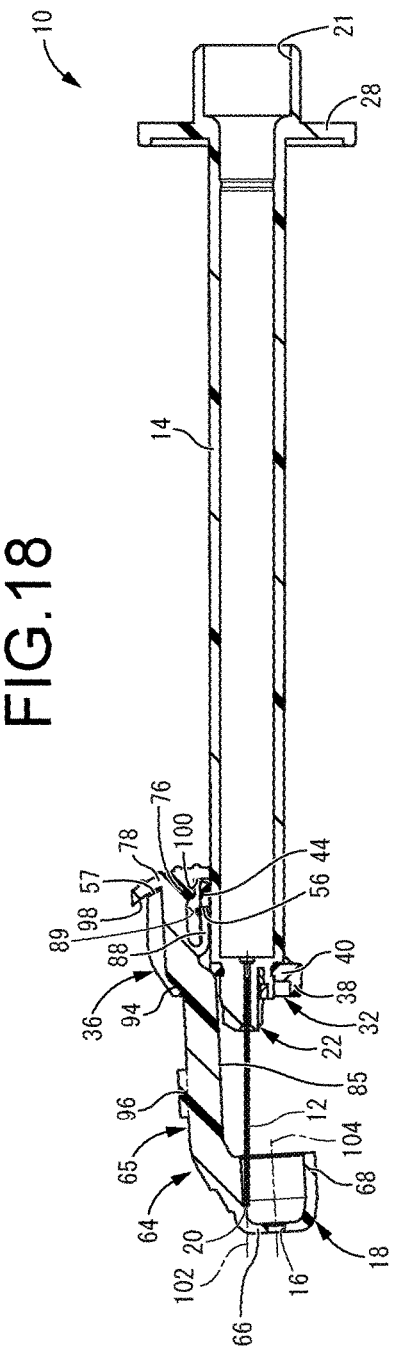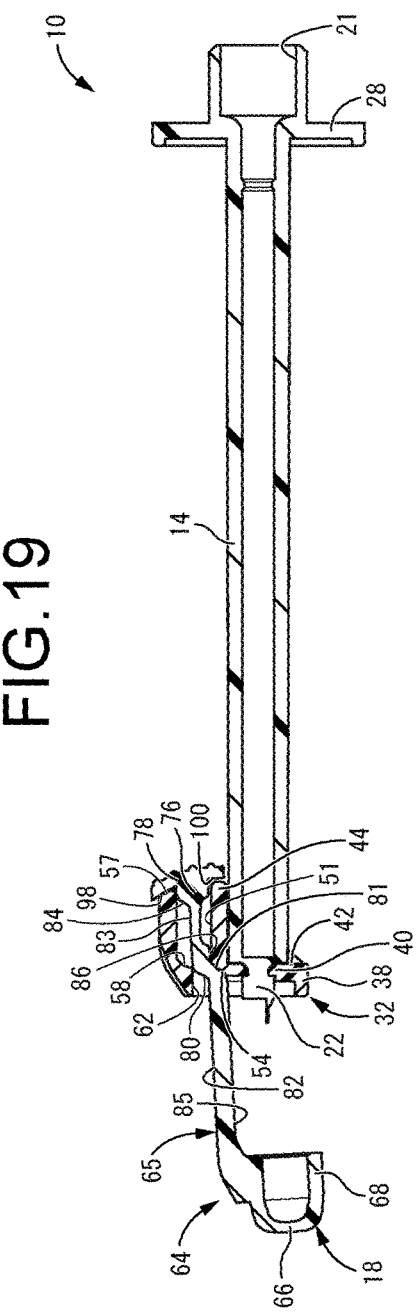

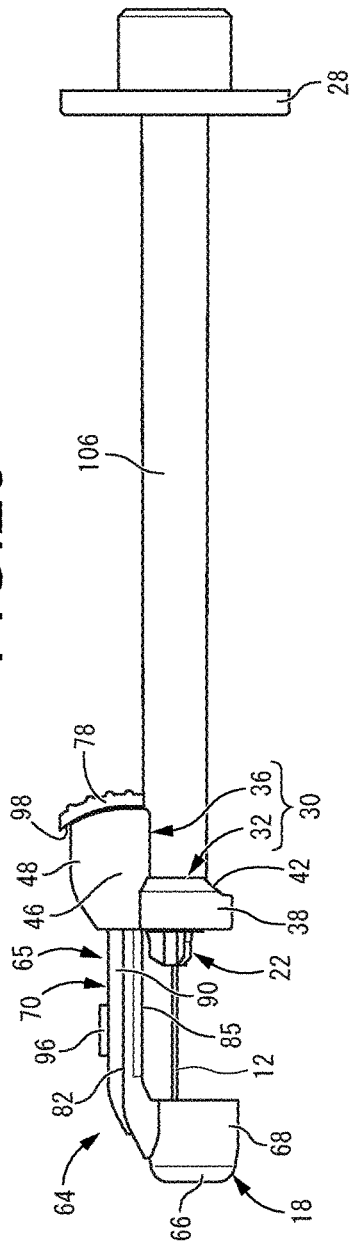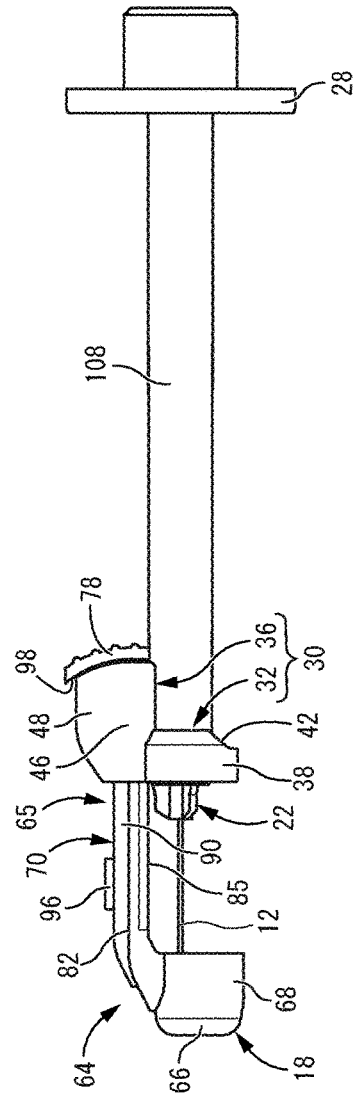

NEEDLE ASSEMBLY

TECHNICAL FIELD

The present invention relates generally to a needle assembly, and more particularly, to a needle assembly equipped with a mechanism for protecting a needle tip by means of a needle tip cover after use.

BACKGROUND ART

Conventionally, in the medical field, when injecting drug solution or the like into the patient, or proceeding fluid transfusion, blood transfusion, artificial dialysis, blood collection or the like for the patient, a needle assembly equipped with a hollow or solid needle for puncturing has been used as a medical instrument for the procedure. Such a needle assembly typically has a structure in which the needle projects from a needle hub. As the needle hub, for example, a needle base attached to a male luer of a syringe, an inner needle hub, a syringe hub integrally formed with a distal end of the syringe are employed so as to provide needle assemblies with various types of structures for use in various procedures.

Meanwhile, after using the needle assembly, if the removed needle tip is left exposed, there is a risk that inadvertent pricking accidents may occur where physicians, nurses, or disposal contractors might mistakenly prick their fingers or the like with the exposed needle tip. Once such an inadvertent pricking accident occurs, there is a risk of infectious diseases transmitted by the blood adhered to the needle tip, or inadvertent ingestion of the drug solution adhered to the needle tip.

Thus, a needle assembly provided with a needle tip cover for covering the needle tip after use has been suggested. For example, Japanese Domestic Publication of International Patent Application No. JP-A-2005-501665 (Patent Document 1) describes such needle assembly for which, after use of the needle assembly, a cap externally disposed about a needle is configured to be moved to the distal end side of the needle so as to cover the needle tip. Also, when the needle tip is covered by the cap, the needle tip is configured to be deviated from the needle through-hole to the direction of eccentricity to be covered so that the needle tip is not seen through the needle through-hole of the cap.

However, with the needle assembly of conventional construction described in Patent Document 1, in order to cover the needle tip by deviating it from the needle through-hole, the cap is connected with the syringe main body by an elastically deformable member, so that the cap is urged in the direction of eccentricity with respect to the injection needle all the time. Therefore, while the cap is moved to the distal end side of the needle after use of the needle assembly, the inner surface of the through hole of the cap pressed against the side surface of the injection needle almost scrapes the outer surface of the injection needle.

Consequently, the blood, drug solution or the like adhered to the outer surface or the distal end of the injection needle is scraped off while the cap is moved to the distal end side of the needle, and is likely to be left adhered on the surface of the cap covering the needle tip. Accordingly, there is a risk that the blood, drug solution or the like adhered to the surface of the cap may be further transmitted to other medical instruments or the fingers or the like of the nurses, or scatter around.

BACKGROUND ART DOCUMENT

Patent Document

Patent Document 1: JP-A-2005-501665

SUMMARY OF THE INVENTION

Problem the Invention Attempts to Solve

The present invention has been developed in view of the above-described matters as the background, and it is an object of the present invention to provide a needle assembly with a novel structure which is able to, when covering the needle tip with the needle tip cover after use, cover the needle tip with the needle tip cover through a simple operation while preventing the blood or the like adhere to the outer circumferential surface of the needle from adhering to the surface of the needle tip cover.

Means for Solving the Problem

A first mode of the present invention provides a needle assembly including: a needle projecting from a needle hub; and a needle tip cover having a needle hole into which the needle is inserted, the needle tip cover being externally provided about the needle so as to be movable in a needle axis direction and configured to cover a needle tip by being moved to a distal end side beyond the needle tip, the needle assembly being characterized in that: the needle hole has an inside diameter dimension larger than an outside diameter dimension of the needle; a fixed-side guide is fixedly provided to the needle; a moving-side guide is integrally provided to the needle tip cover; and the moving-side guide is engaged with the fixed-side guide so as to provide a guide mechanism to guide the needle tip cover from a proximal end side of the needle toward the distal end side thereof while keeping the needle tip cover noncontact with the needle and, at a position beyond the needle tip, to deviate the needle tip cover in a direction in which the needle hole goes away from a center axis of the needle so as to avoid contact of the needle tip with the needle hole while guiding the needle tip cover to a position where the needle tip cover covers the needle tip.

With the needle assembly constructed according to the present mode, while the needle tip cover moves to the position where the needle tip is covered, the needle and the needle hole are kept noncontact. Thus, the blood, drug or the like adhered to the distal end or the outer circumferential surface of the needle will be prevented from being scraped by the needle tip cover and adhering to the surface of the needle tip cover. This will effectively avoid the problem of re-adhesion of the blood to the other medical instruments or the fingers or the like of the nurses caused by the adhesion of the blood or the like to the surface of the needle tip cover.

Moreover, at the position where the needle tip is covered, the needle tip cover is deviated in the direction in which the needle hole goes away from the center axis of the needle. Thus, the needle tip to which the blood or the like is likely to adhere is effectively covered by the needle tip cover, thereby excellently preventing the blood adhered to the needle tip from scattering around. Besides, even if an external force is exerted on the needle tip cover at the position where the needle tip is covered, since the position of the needle tip is deviated from the center hole of the needle tip cover, the needle tip will never be exposed by an accidental return of the needle tip cover. Furthermore, while it is difficult to apply the conventional art to a fine needle because the load is exerted on the needle when the needle tip is deviated from the needle through-hole in the direction of eccentricity, with the present mode, the needle hole and the needle will not contact with each other while movement of the needle tip cover, so that even if applied to a fine needle, the needle never breaks while movement of the needle tip cover.

A second mode of the present invention provides the needle assembly according to the first mode, wherein the guide mechanism is configured to guide the needle tip cover toward the distal end side in a direction inclined with respect to the center axis of the needle so as to deviate the needle tip cover in the direction in which the needle hole goes away from the center axis of the needle.

With the needle assembly constructed according to the present mode, the needle tip cover is guided in the direction inclined with respect to the center axis of the needle. Thus, in the operation of moving the needle tip cover from the proximal end side to the distal end side, it is possible to deviate the needle tip cover in the direction in which the needle hole goes away from the center axis of the needle without considerably changing the direction of exertion of the operating force, thereby improving ease of operation.

A third mode of the present invention provides the needle assembly according to the first or second mode, wherein the fixed-side guide includes a guiding groove extending in the needle axis direction, the moving-side guide includes an elongated guiding rod to be guided by the guiding groove, the guiding groove of the fixed-side guide and the guiding rod of the moving-side guide include respective stepped parts, and the needle tip cover is configured to be moved in the direction in which the needle hole goes away from the center axis of the needle by the guiding rod being guided and moved with respect to the guiding groove toward the distal end side of the needle in the needle axis direction so that the stepped part of the guiding rod reaches a position of the stepped part of the guiding groove.

With the needle assembly constructed according to the present mode, the guiding groove and the guiding rod include the respective stepped parts. Thus, by the both stepped parts acting in cooperation with each other, the needle tip cover is moved in the direction in which the needle hole goes away from the center axis of the needle. This makes it possible to more reliably move the needle tip cover in the direction in which the needle hole goes away from the center axis of the needle.

A fourth mode of the present invention provides the needle assembly according to the third mode, wherein the guiding rod is inserted into the guiding groove so as to be guided in the needle axis direction, and the guiding rod on the distal end side of the needle beyond the stepped part extends straightly in the needle axis direction.

With the needle assembly constructed according to the present mode, the guiding rod extending straightly in the needle axis direction is inserted into the guiding groove extending in the needle axis direction. This makes it possible to minimize play of the guiding rod within the guiding groove. Operating force can be stably exerted on the guiding rod thereby.

A fifth mode of the present invention provides the needle assembly according to any of the first through fourth modes, wherein the needle tip cover is configured to move translationally in the direction in which the needle hole goes away from the center axis of the needle without tilting with respect to the needle at the position beyond the needle tip.

With the needle assembly constructed according to the present mode, the needle tip cover is deviated in the direction in which the needle hole goes away from the center axis of the needle while moving translationally without tilting with respect to the needle. Thus, it is possible to stably exert the external force for moving the needle tip cover without considerably changing the direction of the operating force exerted on the guiding rod, thereby improving ease of operation.

A sixth mode of the present invention provides the needle assembly according to any of the first through fifth modes, wherein the fixed-side guide includes a guiding groove extending in the needle axis direction, the moving-side guide includes an elongated guiding rod to be guided by the guiding groove, and a completed-position locking mechanism that prevents the guiding rod from retracting movement to the proximal end side of the needle is provided by the fixed-side guide and the moving-side guide being mutually locked by movement of the needle tip cover to the position where the needle tip cover covers the needle tip.

With the needle assembly constructed according to the present mode, by providing the completed-position locking mechanism, it is possible to avoid the risk of accidental movement of the needle tip cover, so that the needle can be kept protected by the needle tip cover in a more reliable manner. In particular, it is preferable that the completed-position locking mechanism is provided inside the needle assembly so that the user finds it extremely difficult to directly touch the completed-position locking mechanism. This will further prevent unnecessary release of the locking mechanism.

A seventh mode of the present invention provides the needle assembly according to the sixth mode, wherein the completed-position locking mechanism is configured to mutually lock the fixed-side guide and the moving-side guide at the position where the needle tip cover covers the needle tip by the needle tip cover being moved for a prescribed distance further to the distal end side of the needle from the position where the needle tip cover is deviated in the direction in which the needle hole goes away from the center axis of the needle and moved to the position where the needle tip cover covers the needle tip.

With the needle assembly constructed according to the present mode, based on the retraction prevention action for the needle tip cover by the completed-position locking mechanism, the needle tip cover can be more reliably kept in the state where the needle hole is away from the center axis of the needle. Besides, each component can enjoy a high level of allowable error in dimension during manufacture while allowable play for the needle tip cover is sufficiently minimized between the abutting end of the needle tip cover on the advancement side and the position of retraction prevention for the needle tip cover by the completed-position locking mechanism.

Effect of the Invention

The needle assembly constructed according to the present invention is able to prevent blood or the like adhered to the surface of the needle from being scraped by the needle tip cover to be adhered to the surface of the needle tip cover while the needle tip cover is moved to the distal end side of the needle. This will avoid the problem that the blood or the like adhered to the surface of the needle tip cover may be re-adhered to the other medical instruments or the fingers or the like of the nurses.

BRIEF DESCRIPTION OF THE DRAWINGS

FIG. 1 is a top plane view of a needle assembly as a first embodiment of the present invention.

FIG. 2 is a front view of the needle assembly shown in FIG. 1.

FIG. 3 is a cross sectional view taken along line 3-3 of FIG. 1.

FIG. 4 is a cross sectional view taken along line 4-4 of FIG. 1.

FIG. 10 is a top plane view of the needle assembly shown in FIG. 1, depicting the state where a needle tip cover is moved to a position beyond a needle tip.

FIG. 11 is a front view of the needle assembly shown in FIG. 10.

FIG. 12 is a cross sectional view taken along line 12-12 of FIG. 10.

FIG. 13 is a cross sectional view taken along line 13-13 of FIG. 10.

FIG. 16 is a top plane view of the needle assembly shown in FIG. 1, depicting the state where the movement of the needle tip cover is completed.

FIG. 17 is a front view of the needle assembly shown in FIG. 16.

FIG. 18 is a cross sectional view taken along line 18-18 of FIG. 16.

FIG. 19 is a cross sectional view taken along line 19-19 of FIG. 16.

FIG. 20 is a front view of a needle assembly as another embodiment of the present invention, which corresponds to FIG. 17.

FIG. 21 is a front view of a needle assembly as yet another embodiment of the present invention, which corresponds to FIG. 17.

EMBODIMENTS FOR CARRYING OUT THE INVENTION

Figure 5:
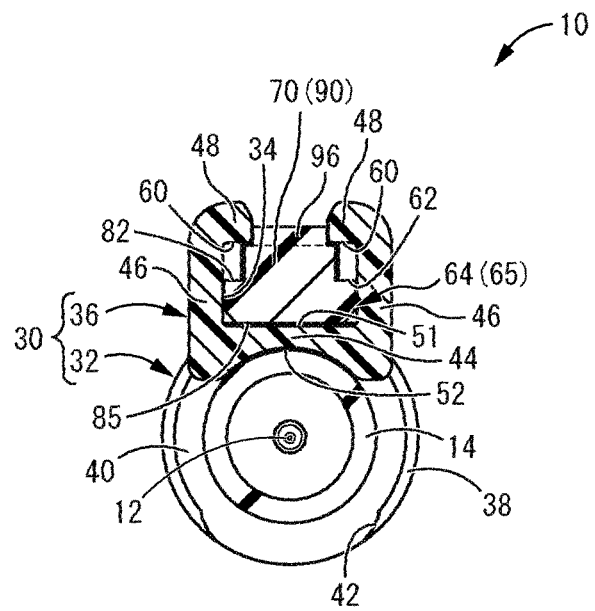
FIG. 5 is an enlarged view of a cross section taken along line 5-5 of FIG. 3.
Figure 6:
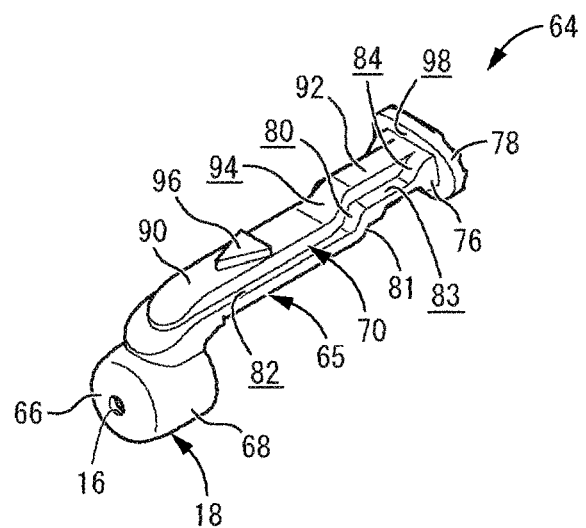
FIG. 6 is a perspective view showing a moving-side guide of the needle assembly shown in FIG. 1.
Figure 7:
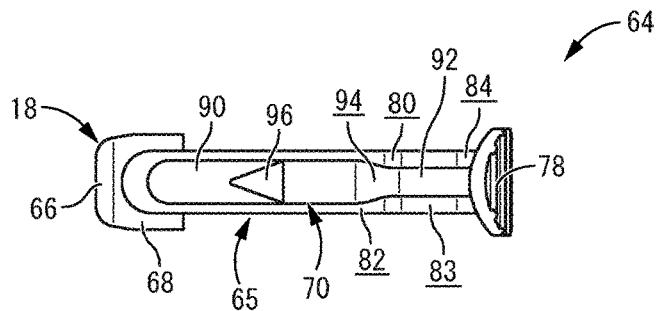
FIG. 7 is a top plane view of the moving-side guide shown in FIG. 6.
Figure 8:
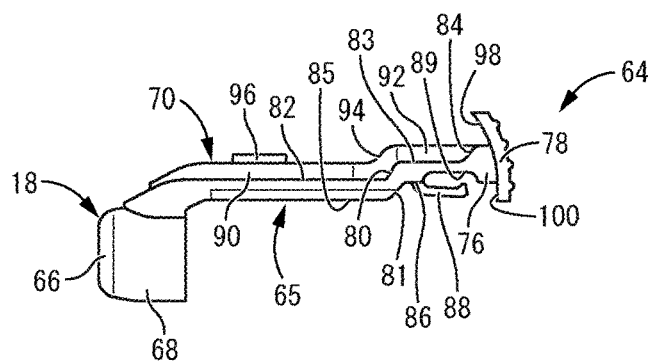
FIG. 8 is a front view of the moving-side guide shown in FIG. 6.
Figure 9:
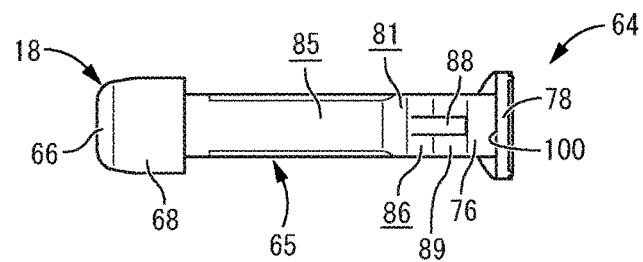
FIG. 9 is a bottom plane view of the moving-side guide shown in FIG. 6.
Figure 14:
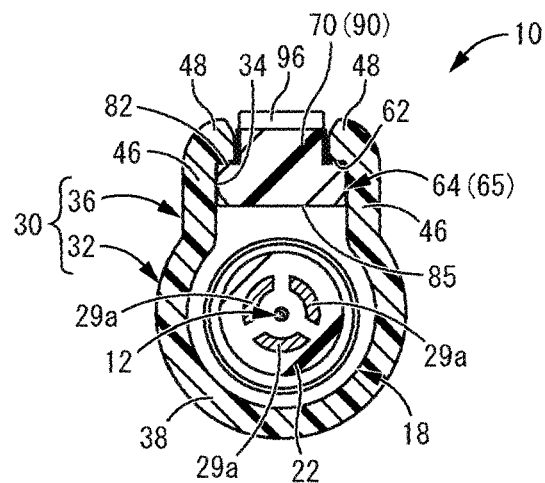
FIG. 14 is an enlarged view of a cross section taken along line 14-14 of FIG. 13.
Figure 15:
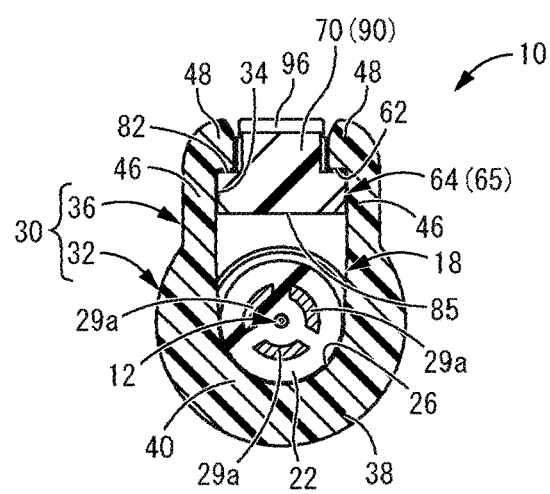
FIG. 15 is an enlarged view of a cross section taken along line 15-15 of FIG. 13.

Embodiments of the present invention will be described below in reference to the drawings.

Referring first to FIGS. 1 through 5, there is depicted a needle assembly 10 according to a first embodiment of the present invention in its initial state before use. The needle assembly 10 includes a needle 12 projecting from a distal end nozzle part of a syringe 14 serving as a needle hub, and a needle tip cover 18 having a needle hole 16 is attached to the needle 12 by being externally provided thereabout. The needle tip cover 18 is movable in the axial direction of the needle 12, namely, the needle axis direction, and configured to cover a needle tip 20 by being moved to the distal end side of the needle 12. In the description hereinbelow, the axial direction of the needle 12 and the syringe 14 refers to the lateral direction in FIG. 1, the distal end side refers to the left side in FIG. 1 on which the needle tip 20 is positioned, and the proximal end side refers to the right side in FIG. 1. Besides, the vertical direction refers to the vertical direction in FIG. 2.

Described more specifically, the syringe 14 constitutes an injection tube of approximately cylindrical shape, and on its proximal end side, provided is a proximal end opening part 21 whose diameter is enlarged, while on its distal end having a bottomed structure, provided is a distal end nozzle part 22 projecting axially outward. In addition, on the outer circumferential surface of the proximal end part of the distal end nozzle part 22, a slot-like constricted section 26 extends in the circumferential direction. Besides, near the proximal end opening part 21 of the syringe 14, a flange part 28 projects from the outer circumferential surface.

Moreover, the proximal end part of the needle 12 is inserted and secured to the center hole of the distal end nozzle part 22 of the syringe 14. The needle 12 is a hollow needle, and in the present embodiment, is made of metal. The needle 12 projects and extends from the distal end side of the syringe 14, and the internal space of the syringe 14 communicates with the external space through the inner hole of the needle 12. Note that on the distal end nozzle part 22, reinforcing pieces 29a, 29b are embedded around its center hole. These reinforcing pieces 29a, 29b are arranged in series in the axial direction, and are each embedded to be secured in the distal end nozzle part 22 with a structure substantially divided into a plurality of pieces in the circumferential direction.

Moreover, a fixed-side guide 30 is externally attached to the distal end portion of the syringe 14. The fixed-side guide 30 includes a joint part 32 of roughly annular shape overall and a guiding part 36 having a guiding groove 34.

The joint part 32 includes a peripheral wall 38 externally fitted onto the distal end nozzle part 22 of the syringe 14, and the peripheral wall 38 is provided with a fixing part 40 projecting from the inner circumferential surface thereof. By the fixing part 40 being mated with the constricted section 26 of the distal end nozzle part 22, the joint part 32 is positioned in the axial direction so as to be externally attached to the distal end nozzle part 22.

The proximal end side of the peripheral wall 38 has a tubular collar structure externally fitted onto the outer circumferential surface of the syringe 14, and is positioned in the axis-perpendicular direction with respect to the outer circumferential surface of the syringe 14. On the proximal end side of the peripheral wall 38, a notch 42 is formed in part of the circumference so that indications marked on the outer circumferential surface of the distal end side of the syringe 14 can be visually observed through the notch 42. Note that in the present embodiment, the joint part 32 is rotatable about the center axis with respect to the syringe 14, so that the position for visually observing the indications through the notch 42 can be suitably changed in the circumferential direction of the syringe 14.

Furthermore, partially on the circumference of the peripheral wall 38, a guiding part 36 is provided so as to extend toward the proximal end side in the axial direction, so that the guiding part 36 is disposed on the outer circumference of the distal end side of the syringe 14. Also, on the upper outer surface of the guiding part 36, the guiding groove 34 is formed so as to extend in the axial direction approximately parallel to the syringe 14. Specifically, the guiding part 36 includes a groove bottom part 44 that constitutes the lower wall part of the guiding groove 34, and side wall parts 46, 46 projecting upward from the groove bottom part 44 on both sides in the width direction (vertical direction in FIG.

1) of the guiding part 36. Besides, on the upper ends of the pair of side wall parts 46, 46, opposite parts 48, 48 are respectively formed so as to project in the direction of opposition (inward in the width direction). Accordingly, the area surrounded by these groove bottom part 44, side wall parts 46, 46, and opposite parts 48, 48 constitutes the guiding groove 34.

Here, since the guiding part 36 is continuously formed on top of the joint part 32, the upper end portion of the peripheral wall 38 constitutes the distal end portion of the groove bottom part 44. Accordingly, as depicted in FIGS. 3 and 4, the connecting portion between the peripheral wall 38 and the groove bottom part 44 constitutes a bent portion 50 which forms a roughly right angle and serves as a stepped part. Also, as depicted in FIGS. 3 through 5, with the groove bottom part 44, a guiding groove bottom face 51 constituting the groove bottom face extends with a flat surface in the axial direction of the syringe 14, while a groove bottom lower face 52 is overlapped on the outer circumferential surface of the syringe 14 with an arcuate shape which curves in the circumferential direction. Moreover, the outer corner face of the bent portion 50 bends diagonally downward from the tip portion of the guiding groove bottom face 51 to the distal end side so as to constitute an inclined lower stepped face 54 straightly extending to the center axis side of the syringe 14.

Besides, the groove bottom part 44 includes a mating window 56 of approximately rectangular shape on its widthwise center portion which is formed so as to perforate the groove bottom part 44 in the thickness direction from the axially medial portion thereof to the bent portion 50. Note that the distal end side of the mating window 56 opens forward in the axial direction on the lower stepped face 54.

Moreover, the end faces on the proximal end side of the side wall parts 46, 46, which extend upward continuously from the end faces on the proximal end side of the groove bottom part 44, constitute proximal end side faces 57, 57 that moderately curves in continuous fashion in the incline direction which progressively goes forward towards the top.

Furthermore, the opposite parts 48, 48 of the guiding groove 34 include stepped parts at their axially medial portion. At the stepped parts, on each lower face of the opposite parts 48, 48 that constitute the upper guiding face of the guiding groove 34, provided is an upper stepped face 58 that inclines diagonally downward as it goes forward. Accordingly, with the upper stepped face 58 interposed in between, a distal-end guiding upper face 62 is positioned below a proximal-end guiding upper face 60 in the step direction (vertical direction in FIG. 4 which coincides with the axis-perpendicular direction). Note that these proximal-end guiding upper face 60 and the distal-end guiding upper face 62 both extend straightly in the axial direction.

By so doing, with the guiding groove 34, the guiding groove bottom face 51 of the lower guiding face is positioned in opposition to the proximal-end guiding upper face 60 of the upper guiding face in the vertical direction, while the lower stepped face 54 of the lower guiding face and the upper stepped face 58 of the upper guiding face are disposed at roughly corresponding positions in the axial direction to be remote from each other in the vertical direction. In other words, the guiding groove 34 includes an opposite lower face and an opposite upper face which are opposed to each other in the axis-perpendicular direction of the needle 12 (vertical direction), where the guiding groove bottom face 51 constitutes the opposite lower face, while the proximal-end guiding upper face 60 and the distal-end guiding upper face 62 constitute the opposite upper face.

Additionally, a moving-side guide 64 depicted in FIGS. 6 through 10 is engaged with the guiding groove 34 of the guiding part 36 of the fixed-side guide 30. The moving-side guide 64 includes an elongated guiding rod 65 and the needle tip cover 18 provided to the distal end portion of the guiding rod 65.

The needle tip cover 18 includes a distal end wall 66 of bottom plate shape and a peripheral wall 68 of roughly cylindrical shape extending from the outer circumferential edge part of the distal end wall 66 to the axially proximal end side, so as to have an approximately cup shape opening to the proximal end side. At the center part of the distal end wall 66, formed is the needle hole 16 passing therethrough in the axial direction with the inside diameter dimension larger than the outside diameter dimension of the needle 12. Note that the inside diameter dimension of the peripheral wall 68 is made larger than the distal end nozzle part 22 provided to the distal end of the syringe 14, so that the needle tip cover 18 covers and caps the distal end nozzle part 22. Meanwhile, the outside diameter dimension of the peripheral wall 68 of the needle tip cover 18 is set such that the peripheral wall 68 fits in the distal end side opening of the peripheral wall 38 of the joint part 32 of the fixed-side guide 30.

Moreover, at the opening edge part of the needle tip cover 18, integrally formed is the elongated guiding rod 65 extending from one location on the circumference to the axially proximal end side. On the guiding rod 65, formed is a center projection 70 that extends on the widthwise center portion of the upper face of the guiding rod 65 in the lengthwise direction and projects upward with a generally constant height dimension. By providing the center projection 70, the height dimension of the guiding rod 65 varies in the width direction so that the widthwise center portion is made thicker than the widthwise both sides. Note that the proximal end portion of the guiding rod 65 is made larger in the cross sectional shape so as to provide a fitting part 76. In addition, at the end of the proximal end side of the fitting part 76, formed is an operating part 78 with a large operating face for operating the moving-side guide 64 by pressing.

Besides, the width dimension of the guiding rod 65 is made approximately equal to or slightly smaller than the width dimension of the guiding groove 34 provided to the fixed-side guide 30. Also, with the guiding rod 65, the height dimension of the portions positioned on the widthwise both sides of the center projection 70 (namely, the portions where the center projection 70 is not provided) is made approximately equal to or slightly smaller than the remote distance between the guiding groove bottom face 51 and the distal-end guiding upper face 62 of the guiding groove 34 in the height direction. Such guiding rod 65 is inserted into the guiding groove 34 of the fixed-side guide 30 and attached thereto in an inserted state in the axial direction.

Also, the axially medial portion of the guiding rod 65 is provided with a stepped part which is bent into a roughly crank, whereby with the stepped part interposed in between, the distal end side of the guiding rod 65 is positioned below the proximal end side thereof so as to approach the syringe 14. Besides, the upper and lower faces of the stepped part respectively constitute inclined faces 80, 81 extending diagonally downward as it goes toward the distal end side in the axial direction.

With the guiding rod 65, each of the lower face of the guiding rod 65 and the upper face of the widthwise both sides where the center projection 70 is not provided, which is configured to make a sliding contact with the inner surface of the guiding groove 34 of the fixed-side guide 30 to be guided in the axial direction, extends straightly to both proximal end side and the distal end side in the axial direction, with the upper inclined face 80 and the lower inclined face 81 interposed in between. Namely, on the upper face of the guiding rod 65, the upper inclined face 80 is connected to a distal end upper face 82 and a proximal end upper face 83 which are both flat. Note that the proximal end part of the proximal end upper face 83 is smoothly connected to the fitting part 76 by an inclined fitting face 84, and the at the fitting part 76, the upper face of the guiding rod 65 constitutes a flat surface with a uniform height over the entire width.

Besides, on the lower face of the guiding rod 65, the lower inclined face 81 is connected to a distal end lower face 85 and a proximal end lower face 86 which are both flat. Moreover, on the widthwise center portion of the proximal end lower face 86, a hooked mating projection 88 is integrally formed projecting from the vicinity of the lower inclined face 81 toward the proximal end side. Also, on the axially medial portion of the proximal end lower face 86 where the mating projection 88 projects, formed is a deformation allowance part 89 recessed in a concave shape. The mating projection 88 projects and is positioned below the lower opening part of the deformation allowance part 89, so that the mating projection 88 is allowed to elastically deform toward inside of the deformation allowance part 89.

Meanwhile, with the center projection 70 projecting from the upper face of the guiding rod 65, the portion from the axial middle to the distal end constitutes a wide part 90 extending straightly with a large width dimension, while the portion from the axial middle to the proximal end constitutes a narrow part 92 extending straightly with a small width dimension. The width dimension of the wide part 90 is made equal to or slightly smaller than the distance between opposed faces of the opposite parts 48, 48 of the fixed-side guide 30 at the portion where the distance is the largest. Meanwhile, the width dimension of the narrow part 92 is made slightly smaller than the distance between opposed faces of the opposite parts 48, 48 at the portion where the distance is the smallest. Besides, on the upper surface of the center projection 70, an inclined face 94 is formed at the lengthwise medial portion, which smoothly connects the faces on the distal end side and the proximal end side of the inclined face 94, which both extend flat. Specifically, with the center projection 70, the narrow part 92 on the proximal end side beyond the inclined face 94 is positioned above the wide part 90 on the distal end side beyond the inclined face 94. Accordingly, the position of the upper face of the wide part 90 is made approximately equal with the position of the proximal-end guiding upper faces 60, 60 of the opposite parts 48, 48.

Therefore, on the axially medial portion of the guiding rod 65, the inclined faces 80, 81, and 94 are formed, while on the axially proximal end portion thereof, the fitting face 84 is provided. By so doing, with the guiding rod 65, the proximal end side beyond each of the inclined faces 80, 81, 84, and 94 is positioned above the distal end side beyond the same. That is, at the axially medial portion of the guiding rod 65, the stepped parts are provided by the inclined faces 80, 81, and 94.

In addition, on the upper face of the center projection 70, an initial stopper 96 is provided projecting upward. In the present embodiment, the initial stopper 96 has a triangular shape in plan view, in which the face on the proximal end side extends in the axis-perpendicular direction, while one apex of the triangle is configured to face to the distal end side. In other words, the width dimension of the initial stopper 96 gradually becomes larger from the distal end side toward the proximal end side. Note that the maximum width dimension of the proximal end side of the initial stopper 96 is made slightly larger than the distance between opposed faces of the opposite parts 48, 48 at the portion where the distance is the smallest.

The operating part 78 is integrally formed with the proximal end side of the guiding rod 65. The operating part 78 has a curving plate shape that curves to be convex to the proximal end side, whose width dimension and length dimension (dimension in the vertical direction in FIG. 2) is made larger than those of the fitting part 76. On the proximal end side face of the operating part 78, irregularities are provided so as to allow the user to easily recognize that he/she is touching the operating part 78. Meanwhile, with the distal end side face of the operating part 78, the face above the fitting part 76 constitutes an upper abutting face 98, and the face below the fitting part 76 constitutes a lower abutting face 100. With these upper and lower abutting faces 98, 100, in correspondence with the proximal end side faces of the proximal end side faces 57 of the opposite parts 48 and the groove bottom part 44 respectively, the upper abutting face 98 has a curved shape, while the lower abutting face 100 has a shape extending in the axis-perpendicular direction.

As to the material of the fixed-side guide 30 and the moving-side guide 64 having configurations described above, a rigid synthetic resin is preferably employed, whereby the needle 12 can be stably protected by the needle tip cover 18.

By the fixed-side guide 30 and the moving-side guide 64 being attached to the syringe 14 with the structure described above, the needle assembly 10 of the present embodiment is constituted. Specifically, the fixing part 40 of the joint part 32 of the fixed-side guide 30 is inserted into the constricted section 26 of the distal end nozzle part 22 of the syringe 14 about the entire circumference in the circumferential direction, so that the fixed-side guide 30 is fixedly attached to the distal end portion of the syringe 14. Note that owing to the fixing part 40 being attached to the constricted section 26 with a certain tightening force, the fixed-side guide 30 is duly positioned with respect to the syringe 14 while being rotatable in the circumferential direction. In the present embodiment, a scale is provided to the syringe 14 on its lower side in the circumferential direction. By aligning the circumferential position of the notch 42 provided to the peripheral wall 38 with the scale, the scale can be read from the outside without being overlapped with the fixed-side guide 30.

Moreover, by the guiding rod 65 of the moving-side guide 64 being inserted into the guiding groove 34 of the guiding part 36 of the fixed-side guide 30, the moving-side guide 64 is attached to the syringe 14. Specifically, in the initial state shown in FIGS. 1 through 5, the needle 12 provided to the distal end of the syringe 14 is concentrically inserted into the needle hole 16 of the needle tip cover 18, and the needle tip 20 of the needle 12 is exposed to outside from the distal end side of the needle tip cover 18, while the distal end nozzle part 22 of the distal end of the syringe 14 is covered by the needle tip cover 18. Note that attachment of the moving-side guide 64 to the guiding groove 34 can be realized by, for example, the side wall parts 46, 46 of the guiding part 36 being pushed to expand to widthwise both sides and the guiding rod 65 being inserted therebetween.

Specifically, by the guiding rod 65 being inserted into the guiding groove 34, as depicted in FIG. 5, the both side surfaces of the guiding rod 65 are in contact with the inner surfaces of the side wall parts 46, 46 of the guiding part 36, while the upper face of the center projection 70 is in contact with the proximal-end guiding upper faces 60, 60 of the opposite parts 48, 48 at the face on the distal end side beyond the inclined face 94.

Moreover, in such initial state, the distal end upper face 82 of the guiding rod 65 is in contact with the distal-end guiding upper faces 62, 62 of the opposite parts 48, 48, while the distal end lower face 85 is in contact with the guiding groove bottom face 51 of the guiding groove 34. Accordingly, the moving-side guide 64, especially the guiding rod 65, is arranged within the guiding groove 34 in a sandwiched state in the vertical direction.

Furthermore, in such initial state, the initial stopper 96 is inserted between the opposite parts 48, 48 which are in opposition to each other. Here, since the maximum width dimension of the initial stopper 96 is made larger than the distance between opposed faces of the opposite parts 48, 48 at the portion where the distance is the smallest, the initial stopper 96 is locked by the opposite parts 48, 48. Accordingly, in the initial state, movement of the moving-side guide 64 to the distal end side with respect to the fixed-side guide 30 is limited. Note that in the initial state, the needle tip cover 18 is inserted in the peripheral wall 38 of the joint part 32, and by the peripheral wall 68 of the needle tip cover 18 being in contact with the fixing part 40 joint part 32, movement of the moving-side guide 64 to the proximal end side with respect to the fixed-side guide 30 is limited.

Then, by puncturing the blood vessel of the patient with the needle 12 of the needle assembly 10, whose syringe 14 is filled with drug solution, and pushing a plunger (not shown) from the proximal end opening part 21, the drug solution will be injected into the blood vessel of the patient via the needle tip 20. After the injection of the drug solution, the health care worker pushes in the moving-side guide 64 toward the distal end side with his/her fingers, so that the moving-side guide 64 is guided toward the distal end side along the guiding groove 34 of the fixed-side guide 30. Accordingly, the needle tip 20 of the needle 12 is configured to be protected by the needle tip cover 18.

Specifically, as depicted in FIGS. 10 through 15, by the moving-side guide 64 being pushed-in toward the distal end side, the initial stopper 96 pushes to expand the opposite parts 48, 48, so that the lock between the initial stopper 96 and the opposite parts 48, 48 is released. By so doing, the moving-side guide 64 is sandwiched in the vertical direction, as well as the narrow part 92 of the center projection 70 is inserted between the opposite parts 48, 48, so that the moving-side guide 64 is displaceable along the guiding groove 34 toward the axially distal end side. Note that with the moving-side guide 64, once the proximal end side portion of the initial stopper 96 displaces beyond the constricted portion between the opposite parts 48, 48 toward the distal end side, the moving-side guide 64 will be unable to return to the initial position.

Besides, by the moving-side guide 64 being displaced to the axially distal end side, the needle tip cover 18 moves to the position beyond the needle tip 20 of the needle 12. That is, the needle tip cover 18 moves until the distal end wall 66 of the needle tip cover 18 is positioned at the distal end side beyond the needle tip 20 of the needle 12. At that time, since the inside diameter dimension of the needle hole 16 is made sufficiently larger than the outside diameter dimension of the needle 12, the needle tip 20 of the needle 12 will be covered by the needle tip cover 18 without the outer circumferential surface of the needle 12 being in contact with the inner circumferential surface of the needle hole 16 during the displacement of the moving-side guide 64 toward the distal end side. In that state, as depicted in FIG. 12, a center axis 102 of the needle 12 and a center axis 104 of the needle hole 16 are coaxially positioned, so that when viewed in the axial direction (when viewed from the left to the right in FIG. 12), the needle tip 20 of the needle 12 is exposed through the needle hole 16.

Here, since the guiding rod 65 of the moving-side guide 64 is fitted in the guiding groove 34 in the vertical and width directions, the displacement of the moving-side guide 64 toward the distal end side is stably realized along the guiding groove 34. That is, after the needle tip cover 18 is moved to the position beyond the needle tip 20 of the needle 12, the moving-side guide 64 is smoothly moved toward the lower left in FIG. 13 along the stepped parts provided to the guiding groove 34 and the moving-side guide 64.

Specifically, when the moving-side guide 64 is pushed-in to the distal end side, first, the proximal end side faces 57, 57 of the opposite parts 48, 48 and the fitting face 84 of the guiding rod 65 of the moving-side guide 64 come into contact. In that state, as depicted in FIG. 13, the lower inclined face 81 of the guiding rod 65 and the lower stepped face 54 which is continuous from the guiding groove bottom face 51 are positioned on roughly the same plane. Accordingly, while the lower inclined face 81 and the lower stepped face 54 are in contact with each other, the moving-side guide 64 moves translationally with respect to the needle 12 along the fitting face 84 toward the lower left in FIG. 13 without tilting with respect to the needle 12. Moreover, at that time, the curving face of the inner surface of the curving upper stepped face 58 of the opposite parts 48, 48 and the upper inclined face 80 of the guiding rod 65 come into contact. Thus, the moving-side guide 64 will be more stably guided toward the lower left in FIG. 13 along the upper stepped face 58. Here, since the fitting face 84, the inner surface of the upper stepped face 58, and the upper inclined face 80 comprise a smooth inclined face or curving face, the moving-side guide 64 will be smoothly guided along the guiding groove 34.

In this way, by the moving-side guide 64 being guided toward the lower left in FIG. 13 along the guiding groove 34, and further pushed to the distal end side, the needle tip cover 18 moves to the completed position, as depicted in FIGS. 16 through 19.

Specifically, the fitting part 76 is fitted into the guiding groove 34 from the proximal end side by the moving-side guide 64 being pushed to the distal end side, while the fitting face 84, the upper inclined face 80, and the lower inclined face 81 are in contact with the proximal end side faces 57, 57 of the opposite parts 48, 48, the upper stepped face 58, and the lower stepped face 54 of the bent portion 50, respectively. Then, the lower inclined face 81 comes into contact with the lower stepped face 54, the proximal end lower face 86 comes into contact with the guiding groove bottom face 51 of the guiding groove 34, and furthermore, the distal end of the proximal end upper face 83 comes into contact with the proximal end of the distal-end guiding upper face 62. In addition, the upper abutting face 98 of the operating part 78 comes into contact with the proximal end side faces 57, 57 of the opposite parts 48, 48, thereby limiting further displacement of the moving-side guide 64 to the distal end side.

Besides, the mating projection 88 provided to the proximal end lower face 86 of the moving-side guide 64 is inserted in the mating window 56 provided to the groove bottom part 44 of the guiding groove 34. By so doing, if an attempt is made to displace the moving-side guide 64 to the proximal end side, the mating projection 88 is configured to strike the proximal end portion of the inner peripheral wall of the mating window 56, thereby limiting displacement of the moving-side guide 64 to the proximal end side. Therefore, in the present embodiment, the mating projection 88 and the mating window 56 provide a completed-position locking mechanism so as to prevent the moving-side guide 64 from movement to the proximal end side by these mating projection 88 and the mating window 56 being mutually locked. Note that when the mating projection 88 is inserted into the mating window 56, a sound will be made so as to notify the user that the moving-side guide 64 is at the completed position by, for example, the mating projection 88 striking the outer circumferential surface of the syringe 14 or the like.

At such movement completed position, by the moving-side guide 64 being guided along the guiding groove 34 toward the lower left in FIG. 18, namely, in the direction inclined with respect to the center axis 102 of the needle 12, the center axis 102 of the needle 12 and the needle hole 16 are deviated. Accordingly, when viewed in the axial direction (when viewed from the left to the right in FIG. 18), the needle tip 20 of the needle 12 is covered by the needle tip cover 18 in the state where the needle tip 20 of the needle 12 is away from the needle hole 16. At that time, the needle 12 and the needle tip cover 18 are kept noncontact from the initial position until just before the moving-side guide 64 moves to the completed position. Note that in the present embodiment, at the movement completed position described above, the distal end side of the moving-side guide 64 slightly inclines downward, so that the center axis 104 of the needle hole 16 inclines with respect to the center axis 102 of the needle 12. That is, the lower end face of the operating part 78 and the outer circumferential surface of the syringe 14 are slightly remote from each other. Also, after the moving-side guide 64 is moved to the completed position, as depicted in FIG. 18, the needle tip 20 of the needle 12 is not in contact, or is slightly in contact with the inner peripheral surface of the peripheral wall 68 of the needle tip cover 18.

Specifically, with the needle assembly 10, a guide mechanism including the fixed-side guide 30 and the moving-side guide 64 is provided so as to guide the moving-side guide 64 along the guiding groove 34 of the fixed-side guide 30 while preventing the needle tip 20 of the needle 12 from being in contact with inner circumferential surface of the needle hole 16 during movement of the moving-side guide 64 from the initial position until just before reaching the completed position. Note that after the moving-side guide 64 is moved to the completed position, the needle tip 20 may be in contact with the needle tip cover 18.

According to the needle assembly 10 of the present embodiment with the structure described above, the needle tip cover 18 moves to the distal end side without any contact between the needle 12 and the needle hole 16 until the distal end wall 66 of the moving-side guide 64 reaches the position beyond the needle tip 20, then the needle tip cover 18 will cover the needle 12. This will avoid the risk that the blood, drug or the like adhered to the needle tip 20 or the outer circumferential surface of the needle 12 may adhere to the inner circumferential surface of the needle hole 16 and scatter to the outside therethrough.

In particular, from such state, the moving-side guide 64 is configured to be deviated in the direction in which the needle hole 16 goes away from the center axis 102 of the needle 12 so as not to expose the needle tip 20 of the needle 12 through the needle hole 16 when viewed in the axial direction. By so doing, even if the blood, drug or the like adhered to the needle tip 20 of the needle 12 might scatter, it is possible to keep the scatter remaining within the needle tip cover 18, thereby more effectively preventing the blood, drug or the like from scattering to the outside through the needle hole 16. Besides, since the needle hole 16 is deviated from the center axis 102 of the needle 12, with the needle 12 covered by the needle tip cover 18, the risk of the needle 12 accidentally sticking out of the needle hole 16 can be avoided.

Also, in the present embodiment, the stepped part is provided to the guiding groove 34, and the stepped part is provided to the guiding rod 65 as well. Accordingly, when the guiding rod 65 moves within the guiding groove 34, through cooperation of the both stepped parts, the guiding rod 65 moves translationally without tilting with respect to the needle 12 in the direction inclined with respect to the axial direction. That is, during operation for pushing-in the moving-side guide 64 from the proximal end side to the distal end side, it is possible to deviate the needle hole 16 from the center axis of the needle 12 without considerably changing the direction of the pushing force. By so doing, the needle tip cover 18 can be moved to the position where the needle 12 is covered with good ease of operation.

Moreover, in the present embodiment, the distal end side of the guiding rod 65 beyond the stepped part is formed in a straight line, and each face that constitutes the distal end side of the guiding rod 65 beyond the stepped part is in contact with the inner surface of the guiding groove 34. This will keep the play of the guiding rod 65 within the guiding groove 34 to a minimum. Accordingly, during operation for pushing-in the moving-side guide 64 to the distal end side, the operating force from the operating part 78 will be stably exerted, thereby improving ease of operation.

Furthermore, in the present embodiment, the mating projection 88 projects from the widthwise center portion of the proximal end lower face 86 of the guiding rod 65, while the mating window 56 is formed on the widthwise center portion of the groove bottom part 44. These mating projection 88 and the mating window 56 constitute the completed-position locking mechanism. This will prevent the moving-side guide 64, which is moved to the completed position, from displacement to the proximal end side, thereby stably keeping the protected state of the needle 12 by the needle tip cover 18. In particular, since the completed-position locking mechanism is provided inside the needle assembly 10 where the user cannot touch directly, the risk of inadvertent release of the locking mechanism is effectively decreased.

Besides, after the moving-side guide 64 is deviated in the direction in which the needle hole 16 goes away from the center axis 102 of the needle 12 along the guiding groove 34, by the moving-side guide 64 being pushed-in further to the distal end side, the operating part 78 comes into contact with the proximal end side faces 57, 57 of the opposite parts 48, 48, as well as the mating projection 88 is inserted into the mating window 56. Then, at that movement completed position, advance and retraction of the moving-side guide 64 become prevented. This makes it possible to avoid the risk that the completed-position locking mechanism works during the deviation of the needle hole 16 from the center axis 102 of the needle 12. In particular, in comparison with the case where the completed-position locking mechanism works just after the deviation of the needle hole 16 from the center axis 102 of the needle 12, the fixed-side guide 30 or the moving-side guide 64 can enjoy a high level of allowable error in dimension during manufacture.

An embodiment of the present invention has been described in detail above, but the present invention shall not be construed as limited in any way to the specific disclosures described above.

For example, whereas the syringe 14 illustrated in the preceding embodiment has an inside volume of 1 mL, the same fixed-side guide 30 and the moving-side guide 64 can also be applied to a syringe 106 depicted in FIG. 20 whose inside volume is 0.5 mL, or a syringe 108 depicted in FIG. 21 whose inside volume is 0.3 mL. Note that in the preceding embodiment, the center axis 104 inclines with respect to the center axis 102 of the needle 12, and the distal end portion of the moving-side guide 64 inclines downward. However, in the modes shown in FIGS. 20 and 21, the center axis of the needle 12 and the center axis of the needle hole are parallel, and the distal end portion of the moving-side guide 64 does not incline downward, so that the lower end face of the operating part 78 and the outer circumferential surface of the syringes 106, 108 are in contact with each other.

Also, whereas in the preceding embodiment, the needle 12 projects from the distal end nozzle part 22 so that the needle hub is a syringe hub which is integral with the syringe, the present invention is not limited to such mode. Specifically, for example, it would also be possible to employ a needle base to be attached to a male luer of a syringe. Moreover, the present invention may be adopted in other medical instruments using a needle such as a prefilled syringe, a blood collection tube holder, a pen needle, or the like. Besides, there is no need for the fixed-side guide to be fixed to the outer circumference of the needle hub as in the preceding embodiment, and could instead be fixed to a syringe barrel, for example. Furthermore, in the preceding embodiment, the fixed-side guide 30 is fixed undetachably to the needle assembly 10 by the fixing part 40 of the fixed-side guide 30 being inserted into the constricted section 26 of the distal end nozzle part 22 of the syringe 14 about the entire circumference in the circumferential direction. However, by giving the fixing part 40 a C-letter shape, for example, the fixed-side guide 30 may be fixed detachably to the needle assembly 10. In such modes, the fixed-side guide and the moving-side guide are attached to these needle hubs so as to constitute the needle assembly according to the present invention.

Moreover, in the preceding embodiment, the guiding groove 34 is provided with the stepped part at its axially medial portion, while the guiding rod 65 is also provided with the stepped part at its axially medial portion, but the present invention is not limited to such mode. For example, the stepped part may also be provided at the axially proximal end portion of the guiding rod. Also, the stepped part may be provided in plurality to each of the guiding groove and the guiding rod. Of course, the stepped part is not essential.

Furthermore, whereas in the preceding embodiment, the guiding groove 34 has a groove shape that opens to two axial ends and above, it may have a through-hole shape that opens only to the two axial ends. In such case, it would also be acceptable that the guiding part is allowed to be opened and closed by being made into a divided structure comprising upper and lower components which are linked by a hinge or the like provided to the lateral side, for example.

Besides, in the preceding embodiment, the upper stepped faces 58, 58 of the opposite parts 48, 48 and the lower stepped face 54 of the bent portion 50 extend toward the lower left in FIG. 13, and the guiding rod 65 is smoothly guided along such guiding groove 34, but the present invention is not limited to such mode. Specifically, it would also be possible for example that the distal end of the opposite parts bends perpendicularly to the proximal end thereof, or the groove bottom part 44 is connected perpendicularly to the fixing part 40 without providing the bent portion 50, or the like, so that the guiding groove bends downward with a stepped shape. In such case, the needle hole can go away from the center axis of the needle by, for example, the moving-side guide being pushed-in from the proximal end side to the distal end side, then further being pushed-in from the upper side to the lower side.

Of course, the direction of deviation of the needle tip cover 18 and the moving-side guide 64 with respect to the needle 12 is not limited to the direction in which they approach the needle 12 in the vertical direction as described in the preceding embodiment, but may be the direction in which they go away from the needle in the vertical direction, for example, or may be any diametrical direction. In preferred practice, as in the preceding embodiment, the needle tip cover 18 and the moving-side guide 64 move so as to approach the needle 12 because the size of the needle assembly 10 will be compact after the movement of the moving-side guide 64 is completed.

Additionally, in the preceding embodiment, after the distal end wall 66 of the needle tip cover 18 is moved to the position beyond the needle tip 20 of the needle 12, the needle tip cover 18 is moved in the direction inclined with respect to the axial direction so that the needle hole 16 goes away from the center axis 102 of the needle 12. However, the present invention is not limited to such mode. Specifically, for example, as long as the needle tip 20 of the needle 12 does not come into contact with the needle hole 16, it would also be acceptable for the needle tip cover 18 to be moved in the direction inclined with respect to the axial direction before the distal end wall 66 of the needle tip cover 18 is moved to the position beyond the needle tip 20 of the needle 12.

Note that after the needle tip cover is moved to the position where the needle tip of the needle is covered, the needle tip or the outer circumferential surface of the needle may be in contact with the inner circumferential surface of the needle tip cover as long as the needle tip does not come into contact with the needle hole.

Also, in the preceding embodiment, regarding the guiding groove 34 and the guiding rod 65, the inner surfaces of the side wall parts 46, 46 of the guiding part 36 and the both side surfaces of the guiding rod 65 are in contact with each other, for example. However, they may alternatively be opposed to each other with a slight distance therebetween as long as there is no substantial play.

Furthermore, modes described hereinbelow are each able to provide a needle assembly with a novel structure in which the guiding rod is less likely to play significantly at the position where the needle tip cover protects the needle tip, and can be recognized as an independent invention capable of solving a different problem from that of the present invention.

A first mode provides a needle assembly including: a needle projecting from a needle hub; and a needle tip cover having a needle hole into which the needle is inserted, the needle tip cover being externally provided about the needle so as to be movable in a needle axis direction and configured to cover a needle tip by being moved to a distal end side beyond the needle tip, the needle assembly being characterized in that: a guiding groove is provided so as to be positioned on an outer circumferential side of the needle hub and extend in the needle axis direction; an elongated guiding rod is provided to the needle tip cover so as to be inserted into the guiding groove and guided in the needle axis direction; the guiding groove and the guiding rod include respective stepped parts; the needle tip cover is configured to be moved in a direction in which the needle hole goes away from a center axis of the needle and to cover the needle tip by the guiding rod being guided and moved with respect to the guiding groove from a proximal end side toward the distal end side of the needle in the needle axis direction so that the stepped part of the guiding rod goes beyond a position of the stepped part of the guiding groove; and a guiding face is provided to the guiding groove so as to guide the guiding rod in the needle axis direction while being in contact with the guiding rod so that at both positions of movement before and after the stepped part of the guiding rod goes beyond the position of the stepped part of the guiding groove, the guiding rod is in contact with and retained by the guiding groove.

With the needle assembly constructed according to the present mode, the guiding rod is configured to be in contact with and retained by the guiding face of the guiding groove before and after going beyond the stepped part of the guiding groove, thereby minimizing play of the guiding rod during movement. In association therewith, the needle hole is prevented from being positioned on the needle axis, so as to decrease the risk that the needle tip cover accidentally moves to the proximal end side and the needle juts out from the needle hole.

A second mode provides the needle assembly according to the first mode, wherein with the guiding groove, the guiding face includes a guiding lower face and a guiding upper face positioned in opposition in a groove depth direction, and the guiding rod is sandwiched and retained between the guiding lower face and the guiding upper face.

A third mode provides the needle assembly according to the first or second mode, wherein the guiding rod further includes a fitting part positioned on a back end side of a direction of movement with respect to the guiding groove and configured to be fitted into a back end side opening of the guiding groove.

A fourth mode provides the needle assembly according to any of the first through third modes, wherein a completed-position locking mechanism that prevents the guiding rod from retracting movement to the proximal end side of the needle is provided by portions of a groove bottom part of the guiding groove and the guiding rod configured to overlap with each other being mutually locked by movement of the needle tip cover to a position where the needle tip cover covers the needle tip.

A fifth mode provides a needle assembly including: a needle projecting from a needle hub; and a needle tip cover having a needle hole into which the needle is inserted, the needle tip cover being externally provided about the needle so as to be movable in a needle axis direction and configured to cover a needle tip by being moved to a distal end side beyond the needle tip, the needle assembly being characterized in that: a fixed-side guide is fixedly provided to the needle; a moving-side guide is integrally provided to the needle tip cover, the moving-side guide being engaged with the fixed-side guide; the fixed-side guide includes a guiding groove extending in the needle axis direction; the moving-side guide includes an elongated guiding rod to be guided by the guiding groove, the guiding rod being inserted into the guiding groove; a portion of the guiding rod to be inserted into the guiding groove and guided in the needle axis direction includes a nonparallel part with respect to the needle axis direction, and by means of the nonparallel part of the guiding rod passing the guiding groove, the needle hole is configured to be guided to a position away from the needle; and the fixed-side guide is given such a size that the moving-side guide is sandwiched and retained by the fixed-side guide in an axis-perpendicular direction of the needle by means of the needle tip cover being moved to a position where the needle tip cover covers the needle tip.

With the needle assembly constructed according to the present mode, play of the needle tip cover will be kept to a minimum at the position where the needle tip cover protects the needle tip, thereby decreasing the risk of the needle hole being positioned on the needle axis. Therefore, even if the needle tip cover accidentally moved to the proximal end side, the needle is prevented from being exposed through the needle hole to cause an inadvertent pricking. Note that as the modes for retaining the moving-side guide by the fixed-side guide when the proximal end portion of the guiding rod is positioned within the guiding groove, preferably employed are a sixth mode or a seventh mode described hereinbelow.

A sixth mode provides the needle assembly according to the fifth mode, wherein the guiding groove includes an opposite lower face and an opposite upper face positioned in opposition in the axis-perpendicular direction of the needle, and by means of the needle tip cover being moved to the position where the needle tip cover covers the needle tip, the guiding rod is configured to be sandwiched and retained between a distal end of the opposite lower face and a distal end of the opposite upper face, and at a proximal end side beyond the distal ends of the opposite lower face and the opposite upper face, the moving-side guide is configured to be sandwiched and retained by the fixed-side guide in the axis-perpendicular direction of the needle. Note that in the present mode, at each position on the distal end side and the proximal end side where the guiding rod is retained by the fixed-side guide, they may be in contact in a dotted way in the needle axis direction.

A seventh mode provides the needle assembly according to the fifth mode, wherein the guiding groove includes an opposite lower face and an opposite upper face positioned in opposition in the axis-perpendicular direction of the needle, and by means of the needle tip cover being moved to the position where the needle tip cover covers the needle tip, the guiding rod is configured to be sandwiched and retained between a distal end side face of the opposite lower face and a distal end side face of the opposite upper face. Note that in the present mode, the upper and lower faces of the guiding groove that retain the guiding rod are configured to be in contact with the guiding rod for a prescribed length in the needle axis direction. Thus, it is acceptable as long as the upper and lower faces for retaining the guiding rod are provided at least at one location in the needle axis direction.

KEYS TO SYMBOLS

10: needle assembly, 12: needle, 14, 106, 108: syringe (needle hub), 16: needle hole, 18: needle tip cover, 20: needle tip, 22: distal end nozzle part (needle hub), 30: fixed-side guide, 34: guiding groove, 44: groove bottom part, 50: bent portion, 56: mating window (completed-position locking mechanism), 57: proximal end side face, 58: upper stepped face, 64: moving-side guide, 65: guiding rod, 80: upper inclined face, 81: lower inclined face, 84: fitting face, 88: mating projection (completed-position locking mechanism), 94: inclined face, 102: center axis (needle 12), 104: center axis (needle hole 16)

The invention claimed is:

1. A needle assembly comprising:
   a needle projecting from a needle hub;
   a needle tip cover having a needle hole into which the needle is inserted and whose inside diameter dimension is larger than an outside diameter dimension of the needle, the needle tip cover being externally provided about the needle so as to be movable in a needle axis direction and configured to cover a needle tip by being moved to a distal end side beyond the needle tip;
   a fixed-side guide fixedly provided to the needle; and
   a moving-side guide integrally provided to the needle tip cover, wherein
   the moving-side guide is engaged with the fixed-side guide so as to provide a guide mechanism to guide the needle tip cover from a proximal end side of the needle toward the distal end side thereof while keeping the needle tip cover noncontact with the needle until the needle tip cover reaches a position beyond the needle tip and, at the position beyond the needle tip, to deviate the needle tip cover in a direction in which the needle hole goes away from a center axis of the needle so as to avoid contact of the needle tip with the needle hole while guiding the needle tip cover to a position where the needle tip cover covers the needle tip.

2. The needle assembly according to claim 1, wherein the guide mechanism is configured to guide the needle tip cover toward the distal end side in a direction inclined with respect to the center axis of the needle so as to deviate the needle tip cover in the direction in which the needle hole goes away from the center axis of the needle.

3. The needle assembly according to claim 1, wherein
   the fixed-side guide includes a guiding groove extending in the needle axis direction,
   the moving-side guide includes an elongated guiding rod to be guided by the guiding groove,
   the guiding groove of the fixed-side guide and the guiding rod of the moving-side guide include respective stepped parts, and
   the needle tip cover is configured to be moved in the direction in which the needle hole goes away from the center axis of the needle by the guiding rod being guided and moved with respect to the guiding groove toward the distal end side of the needle in the needle axis direction so that the stepped part of the guiding rod reaches a position of the stepped part of the guiding groove.

4. The needle assembly according to claim 3, wherein the guiding rod is inserted into the guiding groove so as to be guided in the needle axis direction, and the guiding rod on the distal end side of the needle beyond the stepped part extends straightly in the needle axis direction.

5. The needle assembly according to claim 1, wherein the needle tip cover is configured to move translationally in the direction in which the needle hole goes away from the center axis of the needle without tilting with respect to the needle at the position beyond the needle tip.

6. The needle assembly according to claim 1, wherein
   the fixed-side guide includes a guiding groove extending in the needle axis direction,
   the moving-side guide includes an elongated guiding rod to be guided by the guiding groove, and
   a completed-position locking mechanism that prevents the guiding rod from retracting movement to the proximal end side of the needle is provided by the fixed-side guide and the moving-side guide being mutually locked by movement of the needle tip cover to the position where the needle tip cover covers the needle tip.

7. The needle assembly according to claim 6, wherein the completed-position locking mechanism is configured to mutually lock the fixed-side guide and the moving-side guide at the position where the needle tip cover covers the needle tip by the needle tip cover being moved for a prescribed distance further to the distal end side of the needle from the position where the needle tip cover is deviated in the direction in which the needle hole goes away from the center axis of the needle and moved to the position where the needle tip cover covers the needle tip.

8. The needle assembly according to claim 1, wherein:
   the fixed-side guide includes a guiding groove extending in the needle axis direction,
   the moving-side guide includes a guiding rod to be guided by the guiding groove,
   the guiding groove and the guiding rod include a groove-side inclined face and a rod-side inclined face, respectively, which are configured to be positioned on a plane inclined with respect to the needle axis direction when the needle tip cover is moved to the position beyond the needle tip, and
   the moving-side guide is configured to move to the distal end side in a manner where the groove-side inclined face and the rod-side inclined face are in contact with each other so that the moving-side guide moves translationally without tilting of an axial direction of the needle tip cover with respect to the needle axis direction while moving in the direction in which the needle hole goes away from the center axis of the needle at the position beyond the needle tip.

* * * * *